US010835124B2

(12) United States Patent
Lee et al.

(10) Patent No.: US 10,835,124 B2
(45) Date of Patent: Nov. 17, 2020

(54) POLARIZATION SENSITIVE OPTICAL COHERENCE TOMOGRAPHY APPARATUS AND CONTROL METHOD THEREFOR

(71) Applicant: LG ELECTRONICS INC., Seoul (KR)

(72) Inventors: Jun Lee, Seoul (KR); Jungho Chung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 683 days.

(21) Appl. No.: 15/545,655

(22) PCT Filed: Jun. 3, 2015

(86) PCT No.: PCT/KR2015/005563
§ 371 (c)(1),
(2) Date: Jul. 21, 2017

(87) PCT Pub. No.: WO2016/117775
PCT Pub. Date: Jul. 28, 2016

(65) Prior Publication Data
US 2018/0014730 A1    Jan. 18, 2018

(30) Foreign Application Priority Data

Jan. 22, 2015    (KR) .................. 10-2015-0010754

(51) Int. Cl.
*A61B 5/00*    (2006.01)
(52) U.S. Cl.
CPC .............. *A61B 5/0066* (2013.01); *A61B 5/00* (2013.01); *A61B 5/442* (2013.01); *A61B 2562/0238* (2013.01); *A61B 2562/0242* (2013.01)

(58) Field of Classification Search
CPC ........ G02B 27/283; G02B 1/02; G02B 27/28; G02B 27/286
(Continued)

(56) References Cited

U.S. PATENT DOCUMENTS 7,742,173 B2 * 6/2010 Yun .................... G01N 21/4795
356/479
2012/0136259 A1   5/2012 Milner et al.
(Continued)

FOREIGN PATENT DOCUMENTS

JP    2008272256    11/2008
JP    2014206433    10/2014
KR    1020090093368    9/2009

OTHER PUBLICATIONS

PCT International Application No. PCT/KR2015/005563, International Search Report dated Oct. 20, 2015, 3 pages.

*Primary Examiner* — Mohammed A Hasan
(74) *Attorney, Agent, or Firm* — Lee Hong Degerman Kang & Waimey

(57) ABSTRACT

Disclosed is a polarization sensitive optical coherence tomography apparatus and control method thereof. According to the polarization sensitive optical coherence tomography apparatus and control method thereof of the present invention, the local phase delay value of each layer of a multiple of layers using Jones matrix for a birefringent material having the multiple of layers where each layers optical axis is random based on a polarized signal detected in an optical detector may be calculated. According to the present invention, a skin aging level can be accurately examined by obtaining an accurate accumulated phase delay value for a multiple of layers of birefringent material having a random optical axis.

11 Claims, 8 Drawing Sheets

(58) Field of Classification Search
USPC .......................................... 359/256; 356/256
See application file for complete search history.

(56) References Cited

U.S. PATENT DOCUMENTS

2013/0066215 A1   3/2013  Tearney et al.
2016/0120401 A1*  5/2016  Yamanari ........... G01B 9/02091
                                                   351/206

* cited by examiner

[Fig. 1]
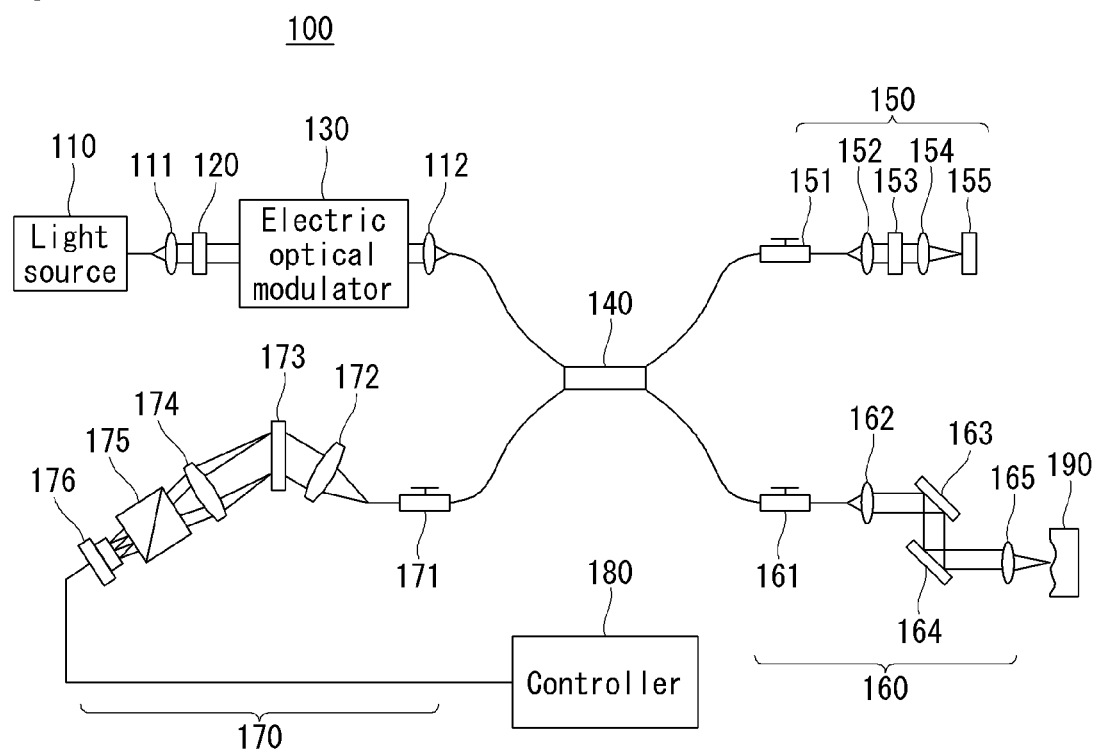

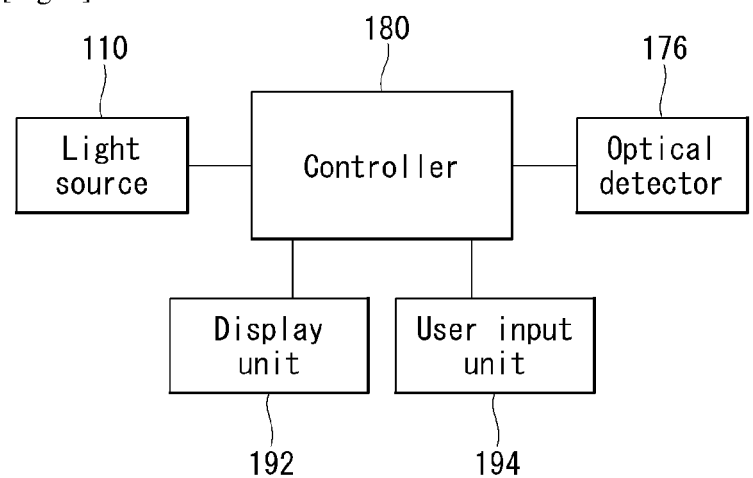
[Fig. 2]

[Fig. 3]
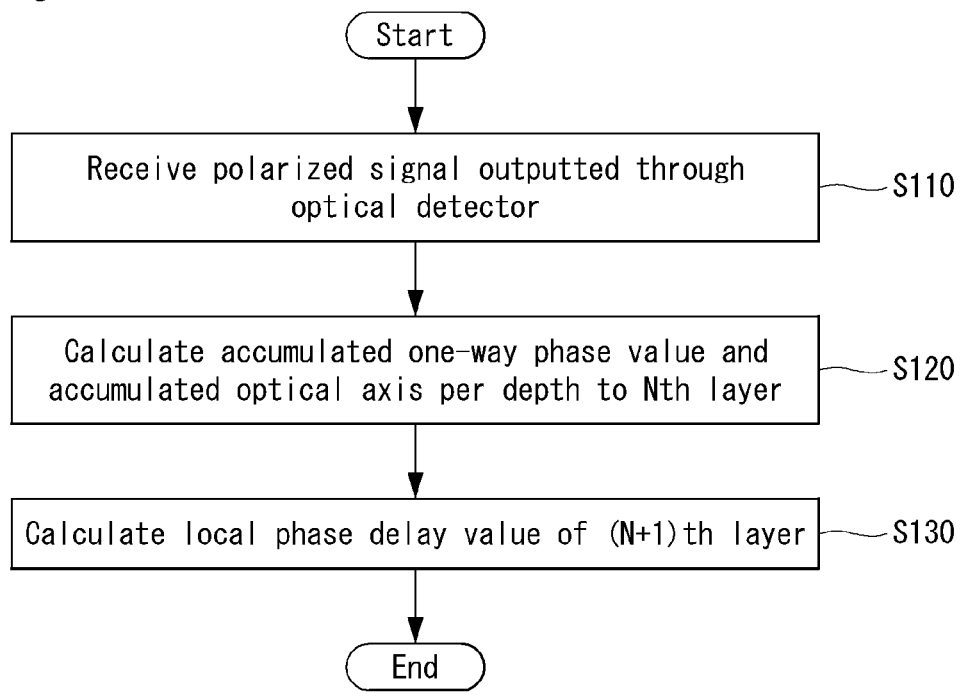

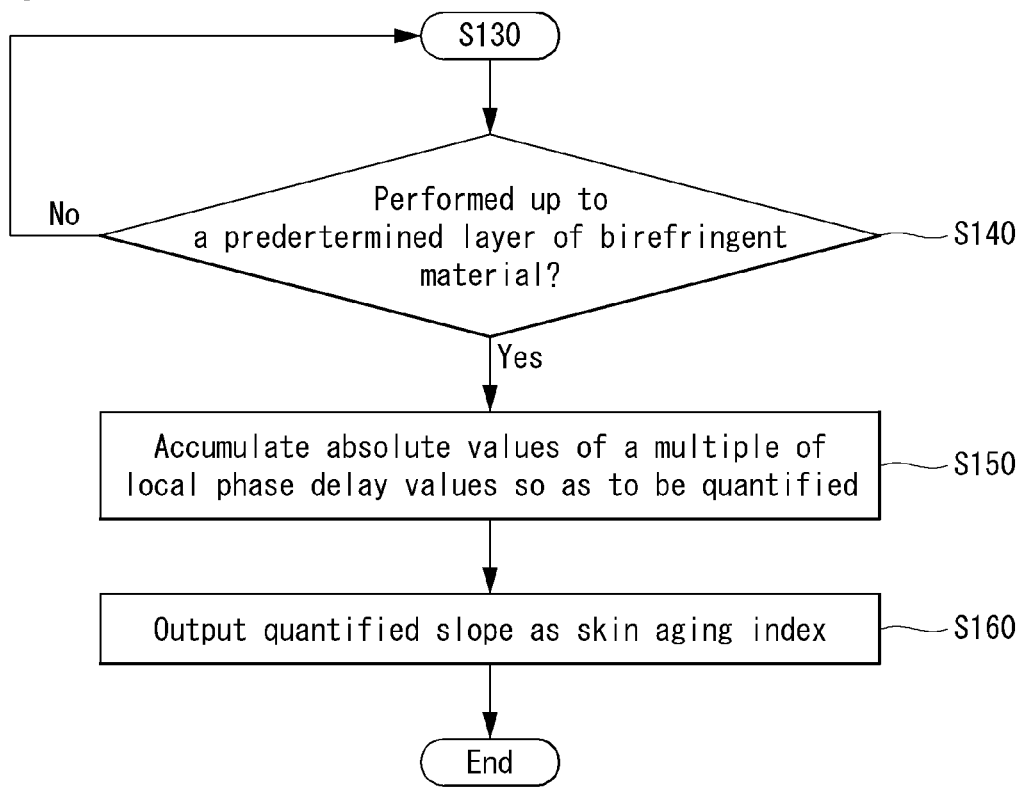
[Fig. 4]

[Fig. 5]
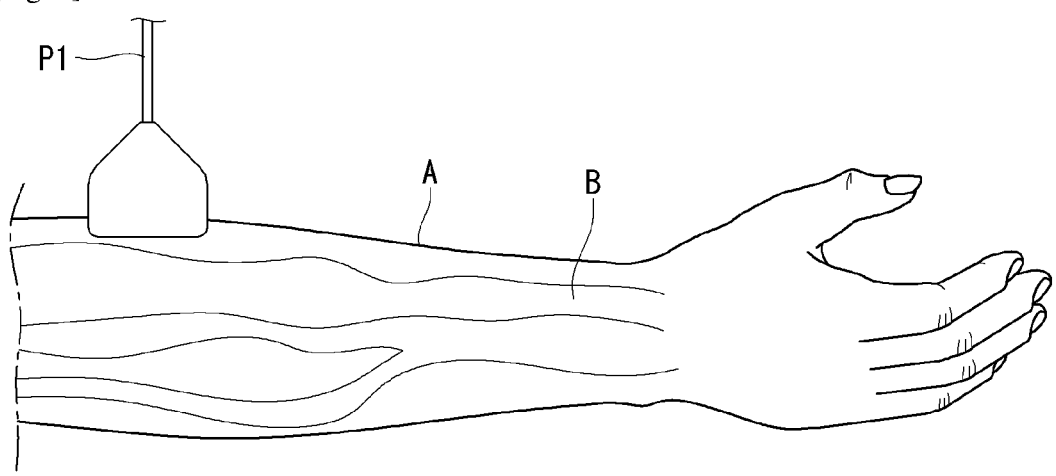

[Fig. 6]
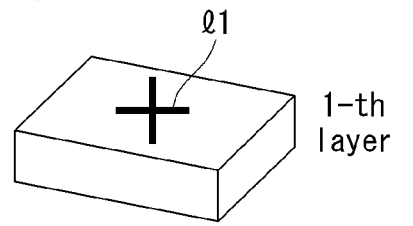 ℓ1 1-th layer
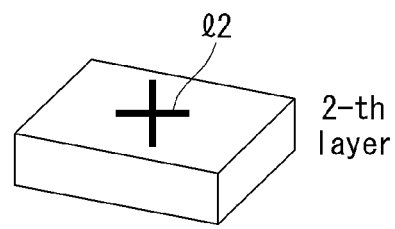 ℓ2 2-th layer
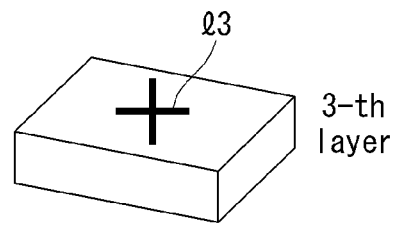 ℓ3 3-th layer
⋮
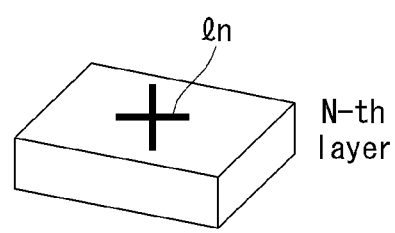 ℓn N-th layer
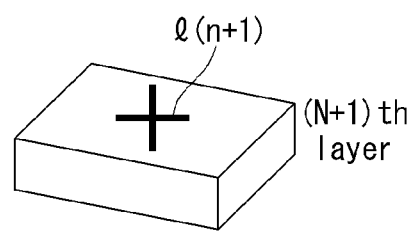 ℓ(n+1) (N+1)th layer
(a)
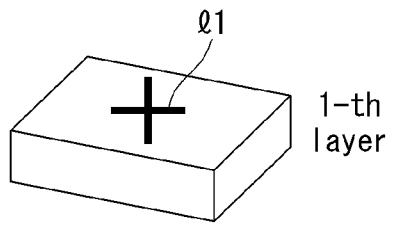 ℓ1 1-th layer
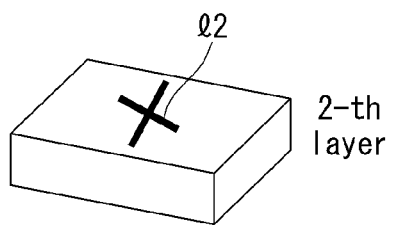 ℓ2 2-th layer
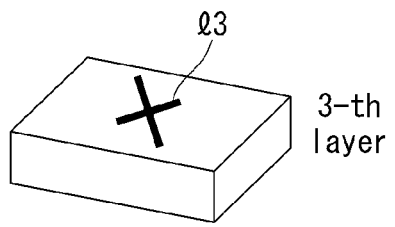 ℓ3 3-th layer
⋮
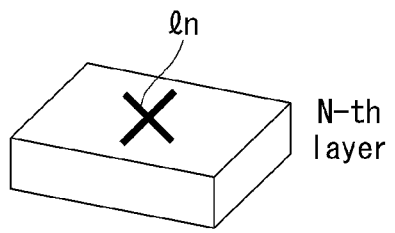 ℓn N-th layer
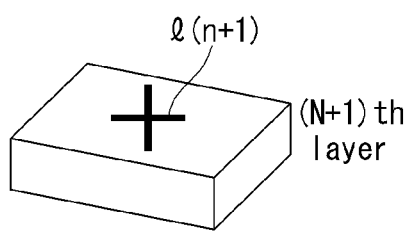 ℓ(n+1) (N+1)th layer
(b)

[Fig. 7]
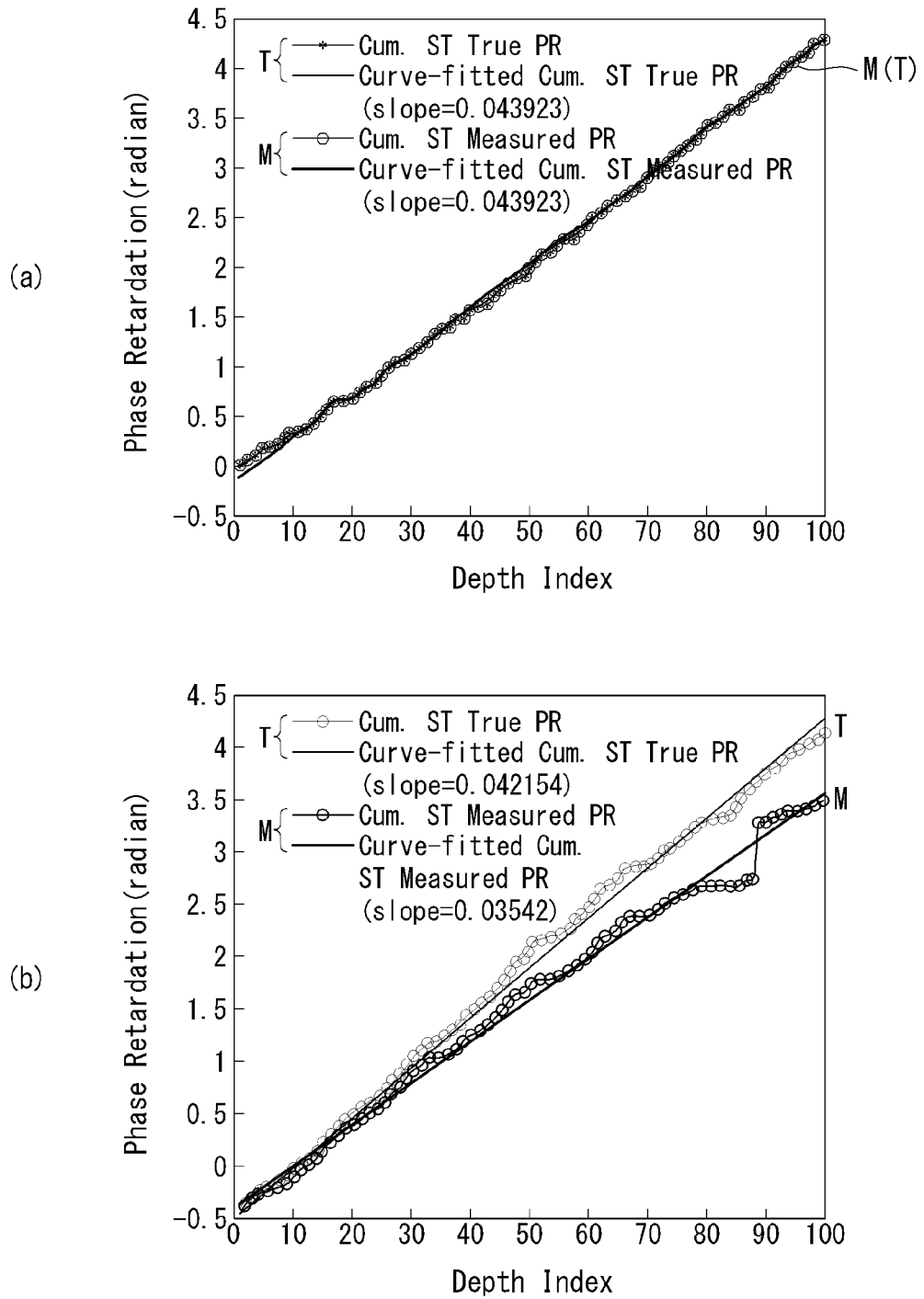

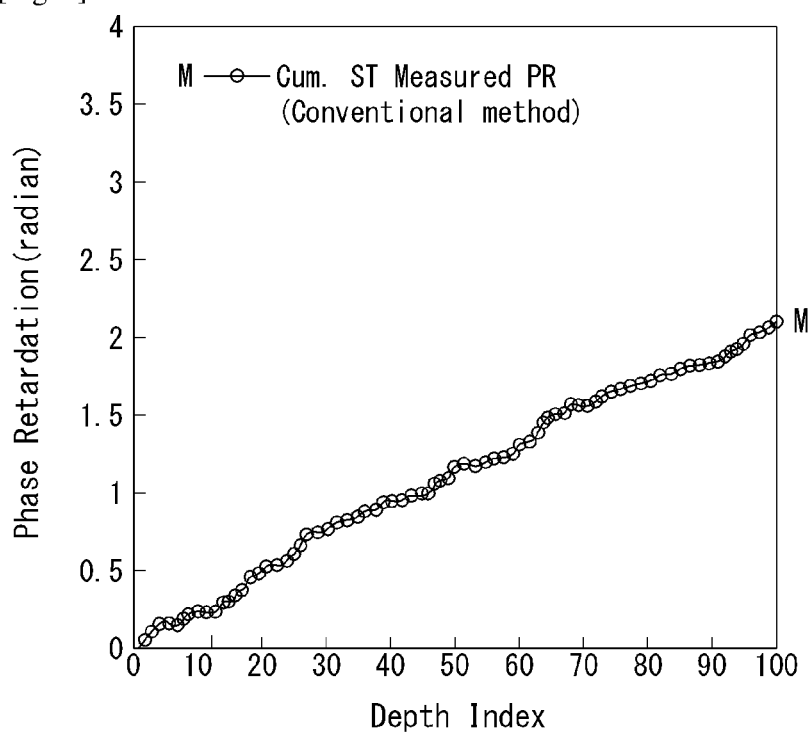
[Fig. 8]

POLARIZATION SENSITIVE OPTICAL COHERENCE TOMOGRAPHY APPARATUS AND CONTROL METHOD THEREFOR

CROSS-REFERENCE TO RELATED APPLICATIONS

This application is the National Stage filing under 35 U.S.C. 371 of International Application No. PCT/KR2015/005563, filed on Jun. 3, 2015, which claims the benefit of earlier filing date and right of priority to Korean Application No. 10-2015-0010754, filed on Jan. 22, 2015, the contents of which are all hereby incorporated by reference herein in their entirety.

TECHNICAL FIELD

The present invention relates to a polarization sensitive optical coherence tomography apparatus for compensating an error according to the coordinate axis of a birefringent material and control method thereof.

BACKGROUND ART

An optical coherence tomography (OCT) apparatus is a tomography apparatus for noninvasively photographing the cross-section of a sample which is given as a micro resolution using the interference characteristic of light. The OCT apparatus is currently used for the clinical purpose for various fields such as ocular science, cardiology, skin science, etc.

The OCT apparatus is used as an apparatus for measuring the structure of the sub-surface of a sample using the intensity of a signal reflected in the sample, but there is a limit in simply recognizing the tissue characteristics of analyzing the state of the organ and distinguishing the normal/abnormal tissue using the intensity of the signal. In order to overcome such a limit, a lot of studies on the polarization sensitive optical coherence tomography (PS-OCT) for providing additional information for recognizing the characteristics of the tissue are currently in progress.

The polarization sensitive optical coherence tomography may be utilized for quantifying the birefractive level to the sample tissue by calculating the phase retardation (PR) between horizontal and vertical elements related to the light incident to the sample tissue. The amount of collagen element, which is the element of the thick skin among the skin tissues, may be quantified and may be utilized as the index of the skin aging by the method of quantifying the birefractive level.

Specifically, quantification method of the collagen element has performed quantification with the slope of the absolute value of the cumulative phase natural value using the complex number signal for the skin tissue per depth obtained using the polarization sensitive optical coherence tomography apparatus.

However, the collagen element has the laminated structure where a multiple of layers are stacked, and each layer has a random optical axis, and thus it is a problem that when 0 is generated as the absolute value of the cumulative phase delay value, an inaccurate result is obtained.

DISCLOSURE

Technical Problem

An object of the present invention is to solve the above-mentioned problems and other problems. Further, another object of the present invention is to a polarization sensitive optical coherence tomography apparatus and method of controlling the same which enables the optical axis of each layer to calculate the local phase delay value of each layer using the Jones matrix for a random birefractive material with a multiple of layers based on the polarized signal detected in the optical detector.

Technical Solution

In an aspect of the present invention, a polarization sensitive optical coherence tomography apparatus includes an optical detector and a controller configured to calculate a local phase delay value of each layer using a Jones matrix for a birefringent material having a multiple of layers where an optical axis of each layer is random, based on a polarized signal detected by the optical detector.

The controller may be configured to determine a slope quantified an absolute value of the local phase delay value as a skin aging index.

The controller may be configured to calculate a cumulative optical axis and a cumulative one-way phase delay value per depth having a same optical axis to a Nth layer using one-way Jones matrix and round-trip Jone matrix to the Nth layer and a (N+1)th layer and may be configured to calculate a local phase delay value of the (N+1)th layer using the cumulative optical axis and the cumulative one-way phase delay value per depth having the same optical axis.

The controller may be configured to repeatedly perform a process of calculating the local phase delay value while changing the Nth layer and may be configured to output a slope quantified by accumulating absolute values of a multiple of local phase delay values as a skin aging index.

The controller may be configured to determine a local phase delay value of a next layer using the round-trip Jones matrix to the next layer ((N+1) layer) of the specific layer.

The apparatus may further include a probe contacting skin wherein the controller is configured to deliver incident light outputted from a light source to the skin through the probe, obtain a polarized signal reflected from the skin, and calculate a local phase delay value using the obtained polarized signal.

The optical detector may be formed inside the probe.

The controller may be further configured to detect a depth from the skin surface and a number of layers of a birefringent material to which the incident light has been delivered using the polarized signal obtained through the probe.

The controller may be configured to convert the polarized signal detected by the optical detector into a digital signal so as to be received and may be configured to determine a size and phase value of the digital signal by Fourier-converting each of a vertical polarized signal and horizontal polarized signal of the digital signal.

The apparatus may further include an optical coupler distributing incident light from a light source to a reference arm and a sample arm, respectively.

In another aspect of the present invention, a method of controlling a polarization sensitive optical coherence tomography apparatus includes receiving an outputted polarized signal, which passed through a birefringent material having a multiple of layers where an optical axis of each layer is random, through an optical detector; calculating a cumulative optical axis and a cumulative one-way phase delay value per depth having a same optical axis to a Nth layer using a one-way Jones matrix and round-trip Jones matrix to Nth layer and a (N+1)th layer, and calculating a local phase delay value of the (N+1)th layer using the cumulative optical axis and the cumulative one-way phase delay value per depth having the same optical axis.

Advantageous Effects

The effects of a mobile terminal and method of controlling the same according to the present invention are as follows.

According to at least one of the present embodiments of the present invention, the aging index of the skin may be quantified in consideration of the random optical axis.

Further, according to at least one of the embodiments of the present invention, the tissue may be examined by the non-invasive method and additional information for the tissue characteristics may be provided Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

FIG. 1 illustrates an entire configuration of a PS-OST apparatus according to the present invention.

FIG. 2 schematically illustrates a PS-OST apparatus according to the present invention.

FIGS. 3 to 4 are flowcharts illustrating a method of controlling a PS-OCT apparatus according to the present invention.

FIG. 5 illustrates a use state of a PS-OST apparatus according to the present invention.

FIGS. 6 to 8 illustrate a method of controlling a PS-OST apparatus according to the present invention.

MODE FOR INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

The polarization sensitive optical coherence tomography (PS-OCT) apparatus and method of controlling the same according to the present invention will be specifically described with reference to the attached drawings. It is obvious to one of ordinary skill in the art that the present invention may be embodied into other specific forms within the scope of the spirit and essential features of the present invention.

The PS-OCT apparatus may continually modulate polarized beam from the light source by the E0 modulator (i.e., the polarized modulator or electric optical modulator), divide the continually modulated polarized beam, inject one divided part into the incident beam, obtain the reflected beam, and measure the OCT measurement by the spectrum interference of the reflected beam and the reference beam which is the other divided part of the modulated polarized beam.

Further, the PS-OCT apparatus may obtain the Jones vector or Jones matrix indicating the polarized light characteristic of the sample tissue by simultaneously measuring the vertical polarized light element H and the horizontal polarized element V among spectrum among the spectrum interference elements.

FIG. 1 illustrates an entire configuration of a PS-OST apparatus according to the present invention, and FIG. 2 schematically illustrates a PS-OST apparatus according to the present invention.

Referring to FIG. 1, the PS-OCT apparatus 100 may include a light source 110, a polarizer 120, an E0 modulator 130, an optical coupler 140, a reference arm 150, a sample arm 160, a spectroscope 170, and a controller 180.

The light source 110 uses a super luminescent diode (SLD) having a broadband spectrum or is formed as a pulse laser, and a polarizer 120, an E0 modulator 130, an optical coupler 140, etc. are sequentially connected.

The polarizer 120 may polarize light incident from the light source 110 in a straight line, the E0 modulator 130 can fix a fast axis in the direction of 45 degrees and modulate the inputted voltage so as to continually change the phase difference between the fast axis and a slow axis which is at right angles to the fast axis. According to the configuration, the light incident from the light source 110 may be polarized in a straight manner from the polarizer 120 so as to be incident to the E0 modulator 130 so that the modulation may be performed in the order of the straight polarization, oval polarization, straight polarization, etc. depending on the modulation cycle The optical coupler 140 may diverge the modulated light into a reference arm 150 and a sample arm 160 in the E0 modulator 130.

The reference arm 150 may include a polarization controller 151, a collimate lens 152, a polarizer 153, a condensing lens 154, and a fixed mirror 155.

The sample arm 160 may include a biased controller 161, a collimate lens 162, a fixed mirror 163, a galvano mirror 164, and a condensing lens 165. The beam incident from the optical coupler 140 may be injected by the galvano mirror 164 so as to be irradiated on the sample 190. The reflected light reflected from the sample 190 may be received in the spectroscope 170 with the interference beam by the overlapping with the reference light through the optical coupler 140.

The spectroscope 170 may configured to include a polarized controller 171, a collimate lens 172, a diffraction grating 173, a Fourier conversion lens 174, a polarized beam splitter 175, and an optical detector 176. Here, a CCD camera may be used as an optical detector 176. The interference beam received from the optical coupler 140 may be dispersed as an interference spectrum by the diffraction grating 173 by being collimated by the collimate lens 172. The diffraction grating 173 may convert the dispersed interference spectrum beam into Fourier conversion lens 174 so as to be divided into horizontal and vertical elements with the polarized beam splitter 175 and may be detected through the optical detector 176. The optical detector 176 may detect the phase information of both of the horizontal and vertical polarized signals.

The light source 110, the reference arm 150 and the polarizer 170 may adjust the initial polarized state of each beam sent from the light source 110 by the installation of each polarized controller. The polarized state, which is continually modulated with the E0 modulator 130, is maintained as the relation of the polarized state in a constant state with constant amplitude in the reference light and the object light, and the polarizer 170 connected to the optical coupler 140 may be controlled to maintain the constant amplitude and the constant polarized state.

When correcting the polarizer 170, the peak locations of the horizontal polarized signal and the vertical polarized signal may be adjusted to be the same by stopping the E0 modulator 130, blocking the reference light and putting the slide glass and the reflex mirror in the sample arm 160. Further, the OCT signal is detected in the polarizer 170 from the backside of the slide glass and the reflex mirror, and the peak phase of the OCT signal may be monitored.

The controller 180 may measure the phase delay value of each layer and the optical axis of each layer of birefringent materials having a multiple of layers based on the polarized signal detected in the optical detector 176. The controller 180 may calculate the local phase delay value of each layer for birefringent materials, in which the optical axis of each layer is random, using the Jones matrix.

At this time, the controller 180 may convert the polarized signal detected in the optical detector 176 into a digital signal so as to be received and may determine the size and phase value by Fourier-convert the vertical polarized signal and the horizontal polarized signal of the digital signal, respectively.

The controller 180 may determine the slope having quantified the absolute value of the local phase delay as the skin aging index. Hence, according to the present invention, the skin aging index may be outputted as the quantitative number. The greater the quantitative number is, the greater collagen the skin tissue contains, and thus it may be understood that the skin aging level is relatively low.

Specifically, the controller 180 may calculate the cumulative polarized phase delay value and the cumulative optical axis per depth having the same optical axis to Nth layer using one-way polarized Jones matrix and round-trip Jones matrix to Nth layer and (N+1)th layer. Namely, the controller can calculate the cumulative one-way phase delay value and cumulative optical axis per depth on the assumption that respective optical axes of a multiple of layers are the same. When the optical axes of respective layers are different, this value can be an inaccurate phase delay value.

Next, the controller 180 can calculate the local phase delay value of the (N+1)th layer using the cumulative one-way phase delay value and cumulative optical axis per depth having the same optical axis. Specifically, the controller 180 may determine the local phase delay value of the (N+1)th layer using the round-trip Jones matrix to the next layer ((N+1) layer) of a specific layer.

Referring to FIG. 2, the PS-OCT apparatus may further include a display unit 192 and an input unit 194.

The display unit 192 may display a quantified slope value or display the skin state corresponding to the quantified slope value. The display unit 192 may include at least one of a liquid crystal display (LCD), a thin film transistor-liquid crystal display (TFT LCD), an organic light-emitting diode (OLED), a flexible display, and a 3D display.

The user input unit 194 may generate input data for operation control of the polarization sensitive optical coherence tomography apparatus. The input unit may be configured with a key pad, a dome switch, a touch pad, a jog wheel, and a jog switch.

Further, the optical detector of the PS-OST apparatus is formed inside the probe, the incident light outputted from the light source is delivered from the light source to the skin through the probe, and the polarized light signal reflected from the skin may be obtained.

The controller 180 may further detect the depth from the skin surface the number of layers of the birefrigent materials to which the incident light has been transmitted using the polarized signal obtained through the probe.

FIGS. 3 to 4 are flowcharts illustrating a method of controlling a PS-OCT apparatus according to the present invention.

In the controller 180, there may a multiple of layers, the optical axis of each layer may pass a random birefringent material, and a polarized signal outputted through the optical detector 176 may be received (S110).

Specifically, the controller 180 may convert the polarized signal detected in the optical detector 176 into a digital signal and receive the converted signal and determine the size and phase value by Fourier-converting each of the vertical polarized signal and the horizontal polarized signal.

Next, the controller 180 may calculate the cumulative one-way phase delay value and the cumulative optical axis per depth having the same optical axis per the Nth layer using the one-way polarized Johns calculus and the round-trip Jones matrix to the Nth layer and (N+1)th layer (S120).

Specifically, the controller 180 may express Jones matrix related to the Nth sub-material layer as the linear retarder like [Equation 1]. At this time, the sub-material needs the precondition that the intensities and reducing ratios of the horizontal element signal and the vertical element signal of the incident light are the same, and when the thickness of the sample is small, the difference of the attenuation ratio is not generated, and thus when the collagen of the skin is used as the sub-material, it is not a problem.

$$J_n = J_L(\alpha_n, \delta_n) = R(\alpha_n) \Lambda(\delta_n) R(-\alpha_n) \quad \text{[Equation 1]}$$

Here, $R(\alpha_n)$ indicates the coordinate axis rotation matrix and $\Lambda(\delta_n)$ indicates the phase delay matrix between the horizontal element signal and the vertical element signal, which are shown in Equation 2 below.

$$R(\alpha_n) = \begin{pmatrix} \cos(\alpha_n) & -\sin(\alpha_n) \\ \sin(\alpha_n) & \cos(\alpha_n) \end{pmatrix} - (1) \quad \text{(Equation 2)}$$

-continued $$\Lambda(\alpha_n) = \begin{pmatrix} e^{i\delta n/2} & 0 \\ 0 & e^{i\delta n/2} \end{pmatrix} \quad \text{-②}$$

Further, the cumulative single-trip (ST) Jone matrix $J_{ST}(n)$ of from the first layer to the Nth layer is the multiple of the linear retarder related to each layer, which may be shown as Equation 3 below.

$$J_{ST}(n) = J_n J_{n-1} \ldots J_1 \quad \text{(Equation 3)}$$
$$= R(\phi_n) R(\beta_n) \Lambda(k_n) R(-\beta_n)$$
$$= R(\phi_n) J_L(\beta_n, k_n)$$

Here, $R(\varphi_n)$ indicates the optical axis rotation formed by the multiplication of the Jones matrix related to sub-material layers having different optical axes of from the first layer to the Nth layer, and $J_L(\beta_n, k_n)$ indicates the linear retarder having the cumulative phase delay value $\beta_n$ and cumulative optical axis $k_n$ formed by the multiplication of the Jones matrix related to sub-materials layers having the same optical axis.

$R(\varphi_n)$ is a value which cannot be directly measured in the PS-OCT apparatus, but the equation where $R(\varphi_n)$ is removed in the cumulative round-trip Jones matrix $J_{RT}(n)$ of from the first layer to the Nth layer can be obtained as in Equation 4 below by the transpose symmetric characteristic of $J_{RT}(n)$.

$$J_{RT}(n) = (J_n J_{n-1} \ldots J_1)^T J_n J_{n-1} \ldots J_1 = J_L(\beta_n, 2k_n) \quad \text{[Equation 4]}$$

The cumulative phase delay value $\beta_n$ and cumulative optical axis $k_n$ of from the first layer to the Nth layer can be calculated using equation 1 and equation 4 through PS-OCT apparatus.

Further, (N+1)th local phase delay value can be calculated like Equation 6 using Equation 5 which is the cumulative round-trip Jones matrix to the (N+1)th layer.

$$J_{RT}(n+1) = (J_{n+1} J_n \ldots J_1)^T J_{n+1} J_n \ldots J_1 \quad \text{(Equation 5)}$$
$$= [R(\phi_n) J_L(\beta_n, k_n)]^T J_{n+1}^T J_{n+1} [R(\phi_n) J_L(\beta_n, k_n)]$$
$$= J_L(\beta_n, k_n)^T [R(\phi_n)^T J_{n+1}^T J_{n+1} R(\phi_n)] J_L(\beta_n, k_n)$$
$$= J_L(\beta_n, k_n)^T [R(-\phi_n) J_{n+1}^T J_{n+1} R(\phi_n)] J_L(\beta_n, k_n)$$

$$(J_{n+1}) = J_L^{-1}(\beta_n, k_n) J_{RT}(n+1) J_L(\beta_n, k_n) \quad \text{(Equation 6)}$$
$$= R(-\phi_n) J_{n+1}^T J_{n+1} [R(\phi_n)]$$

Here, J(N+1) and the round-trip Jones matrix of (N+1)th layer have a similar conversion relation, and thus phase delay value of the (N+1)th layer may be obtained using the Eigenvalue of the J(N+1) matrix.

Finally, the controller 180 may calculate the local phase delay value of the (N+1)th layer using the cumulative optical axis and the cumulative one-way phase delay value per depth having the same optical axis (S130).

The controller may express the cumulative Jones matrix of $z_{ref}$ layer to z layer for the sample tissue like Equation 7.

$$J_{RT}(Z_{ref} \text{ to } Z) = J(z) J(z_{ref})^{-1} = \begin{bmatrix} \eta_H H_{ref}^* & 0 \\ 0 & \eta_V V_{ref}^* \end{bmatrix} \quad \text{(Equation 7)}$$

$$S(z)S(z_{ref})^{-1} \begin{bmatrix} \eta_H H_{ref}^* & 0 \\ 0 & \eta_V V_{ref}^* \end{bmatrix} \text{-①}$$

$$S(z) = \begin{bmatrix} I_1, H(z) & I_2, H(z) \\ I_1, V(z) & I_2, N(z) \end{bmatrix} \text{-②}$$

The i of $I_{i,p}$ indicates the horizontal polarized signal or vertical polarized signal related to the first or second incident beam, $H_{ref}$ and $V_{ref}$ indicate the horizontal polarized signal or vertical polarized signal of the detected reference arm, and $\eta_H$ and $\eta_V$ indicate the quantum efficiency which is generated by dividing the responsibility of each horizontal polarized signal and vertical polarized signal by the number of photons.

Further, Equation 8 may be shown by applying Equation 7 to Equation 4, and the cumulative polarized phase delay value ($\delta_z$) and cumulative optical axis value ($\theta_z$) can be indicated as Equation 9 below.

$$J_{RT}(Z_{ref} \text{ to } Z) = \begin{bmatrix} V_{11} & V_{21} \\ V_{12} & V_{22} \end{bmatrix} \begin{bmatrix} \lambda_1 & 0 \\ 0 & \lambda_2 \end{bmatrix} \begin{bmatrix} V_{11} & V_{21} \\ V_{12} & V_{22} \end{bmatrix}^{-1} \quad \text{(Equation 8)}$$

$$\delta_z = \frac{1}{2} tan^{-1} \frac{\text{Im}(\lambda_1 \times \lambda_2^*)}{\text{Re}(\lambda_1 \times \lambda_2^*)}, \quad \text{(Equation 9)}$$

$$\theta_Z = \frac{1}{2} tan^{-1} \frac{2|v_{21} v_{22}| \cos(\tau)}{|v_{22}|^2 - |v_{21}|^2}$$

Here, $\lambda_1$, $\lambda_2$ is a unique value, and ti means the phase difference of $v_{12}$, $v_{11}$.

Hence, the local phase delay value may be obtained by applying the cumulative polarized phase delay value ($\delta_z$) and the cumulative optical axis value ($\theta_z$) to Equation 6.

Referring to FIG. 4, the controller 180 may determine whether the local phase delay value has been obtained to the preset layer of the birefringent material (S140).

When the local phase delay value to the preset layer is obtained (Yes), the controller 180 may accumulate the absolute values of a multiple of local phase delay values so as to be quantified (S150) and output the quantified slope as the skin aging index (S160).

In contrast, when the local phase delay value to the preset layer is not obtained (No), the controller 180 may increase S130 layer (S170) and may repeat the operation.

Namely, the controller may gradually increase the layer from the reference layer, calculate the local phase delay value of each layer, and determine the slope quantified by accumulating the absolute values of respective local phase delay values as the skin aging index. Hence, according to the present invention, the skin aging index may be outputted as the quantified number. The greater the quantified number is, the more collagen the skin tissue contains, and thus it may be determined that the skin aging level is relatively low.

FIG. 5 illustrates a use state of a PS-OST apparatus according to the present invention, and FIGS. 6 to 8 illustrate a method of controlling a PS-OST apparatus according to the present invention.

Referring to FIG. 5, the skin aging level may be measured after locating the probe of the PS-OST apparatus on the skin for measuring the skin aging level.

Specifically, Proble (P1) may be located on the skin surface, the incident light outputted from the light source may be delivered to the skin through the probe (P1), and the polarized signal reflected from the skin may be detected through the probe (P1).

The controller may calculate the local phase delay value of each collagen layer using the reflected polarized signal by passing the collagen (B) contained in the dermis (A).

Referring to FIGS. 6 to 8, when the optical axis of the multi-layer birefringent material is the same ((a) of FIG. 6) and the optical axis is randomly arranged ((b) of FIG. 6), the slopes of the cumulative delay values are differently shown.

Referring to (a) of FIG. 7, when the optical axes of the multi-layer birefringent material are the same ((a) of FIG. 6), the value M calculated y the equation and the actually measured value T are the same within the marge of error.

Referring to (b) of FIG. 7, when the optical axis of the multi-layer birefringent material is random ((b) of FIG. 6), the value M calculated by the equation and the actually measured value T are significantly different.

Referring to FIG. 8, when the optical axis of the multi-layer birefringent material is random ((b) of FIG. 6), the local phase delay value of each layer is calculated, and the calculated value M of the cumulative phase delay value, which is obtained by accumulating the local phase delay values, is the same as 0.0375 [radian/pixel] which is the actual value T within the margin of error.

Hence, according to the present invention, the cumulative phase delay value may be obtained in consideration of the random optical axis for the multilayer birefringent material where the optical axis is random, and thus the inaccuracy by the random optical axis may be removed.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal. This description is intended to be illustrative, and not to limit the scope of the claims. Therefore, the scope of the present invention should not be limited by the embodiments described in this document but should be defined by the appended claims and equivalents thereof.

The invention claimed is:

1. A polarization sensitive optical coherence tomography apparatus comprising:
an optical detector; and
a controller configured to:
calculate a local phase delay value of each layer, of multiple layers, of a birefringent material using a Jones matrix based on a polarized signal detected by the optical detector, wherein an optical axis of each layer of the multiple layers is random;
calculate a cumulative optical axis and a cumulative one-way phase delay value per depth having a same optical axis to a Nth layer using a one-way Jones matrix and a round-trip Jones matrix to the Nth layer and a (N+1)th layer, among the multiple layers of the birefringent material; and
calculate a local phase delay value of the (N+1)th layer using the cumulative optical axis and the cumulative one-way phase delay value per depth having the same optical axis.

2. The apparatus of claim 1, wherein the controller is further configured to determine a slope quantified as an absolute value of the local phase delay value as a skin aging index.

3. The apparatus of claim 1, wherein the controller is further configured to:
repeatedly perform calculating the local phase delay value while changing the Nth layer; and
output a slope quantified by accumulating absolute values of multiple local phase delay values as a skin aging index.

4. The apparatus of claim 3, wherein the controller is further configured to determine a local phase delay value of a next layer using the round-trip Jones matrix to the next layer ((N+1) layer) of a specific layer.

5. The apparatus of claim 1, further comprising:
a probe configured to contact skin,
wherein the controller is further configured to:
provide incident light outputted from a light source to the skin through the probe;
obtain a polarized signal reflected from the skin; and
calculate the local phase delay value using the obtained polarized signal.

6. The apparatus of claim 5, wherein the optical detector is located inside the probe.

7. The apparatus of claim 5, wherein the controller is further configured to detect a depth from a surface of the skin and a number of layers of the birefringent material to which the incident light has been delivered, using the polarized signal obtained through the probe.

8. The apparatus of claim 1, wherein the controller is further configured to
convert the polarized signal detected by the optical detector into a digital signal; and
determine a size and phase value of the digital signal by Fourier-converting each of a vertical polarized signal and a horizontal polarized signal of the digital signal.

9. The apparatus of claim 1, further comprising an optical coupler distributing incident light from a light source to a reference arm and a sample arm.

10. A method of controlling a polarization sensitive optical coherence tomography apparatus, the method comprising:
receiving, through an optical detector, a polarized signal which has passed through a birefringent material having multiple layers, wherein an optical axis of each layer of the multiple layers is random;
calculating a cumulative optical axis and a cumulative one-way phase delay value per depth having a same optical axis to a Nth layer using a one-way Jones matrix and a round-trip Jones matrix to the Nth layer and a (N+1)th layer, among the multiple layers of the birefringent material; and
calculating a local phase delay value of the (N+1)th layer using the cumulative optical axis and the cumulative one-way phase delay value per depth having the same optical axis.

11. The method of claim 10, further comprising:
repeatedly performing calculating the local phase delay value of the (N+1)th layer to a predetermined layer of the birefringent material;
accumulating absolute values of the calculated local phase delay values and quantifying with a slope; and
outputting the quantified slope as a skin aging index.

* * * * *